(12) United States Patent
Jendrucko et al.

(10) Patent No.: US 7,427,417 B2
(45) Date of Patent: Sep. 23, 2008

(54) AROMATHERAPY DELIVERY SYSTEM

(75) Inventors: Mary L. Jendrucko, Torrance, CA (US); Paul J. Jendrucko, Torrance, CA (US)

(73) Assignee: Sequim Lavender Company, LLC, Sequim, WA (US)

( * ) Notice: Subject to any disclaimer, the term of this patent is extended or adjusted under 35 U.S.C. 154(b) by 337 days.

(21) Appl. No.: 11/083,774

(22) Filed: Mar. 17, 2005

(65) Prior Publication Data

US 2005/0207982 A1 Sep. 22, 2005

Related U.S. Application Data

(60) Provisional application No. 60/554,567, filed on Mar. 19, 2004.

(51) Int. Cl.
*A61K 36/00* (2006.01)
*C12M 1/00* (2006.01)

(52) U.S. Cl. ................. 424/725; 424/778; 435/283.1

(58) Field of Classification Search .............. None
See application file for complete search history.

(56) References Cited

U.S. PATENT DOCUMENTS

| | | |
|---|---|---|
| 233,954 A | 11/1880 | Thompson |
| D15,297 S | 8/1884 | Flagg |
| D15,913 S | 3/1885 | Keiser |
| 623,378 A | 4/1899 | McKee |
| 1,327,062 A | 1/1920 | Quinn |
| 1,577,945 A | 3/1926 | Blumenthal |
| 2,112,774 A | 3/1938 | Thorman |
| 2,162,999 A | 6/1939 | Frank |
| 2,342,066 A | 2/1944 | Tramill |
| 2,401,253 A | 5/1946 | Lamb |
| D179,831 S | 3/1957 | Young |
| 2,791,202 A | 5/1957 | Doyle |
| 2,949,611 A | 8/1960 | Wilkaitis |
| 3,105,970 A | 10/1963 | Herzberg |
| 3,260,292 A | 7/1966 | Costello |
| D206,525 S | 12/1966 | Klimkiewicz |
| D206,526 S | 12/1966 | Klimkiewicz |

(Continued)

FOREIGN PATENT DOCUMENTS

JP 08052234 8/1994

(Continued)

*Primary Examiner*—Christopher R. Tate
(74) *Attorney, Agent, or Firm*—Jacques M. Dulin, Esq.; Innovation Law Group, Ltd.

(57) ABSTRACT

An aromatherapy delivery system for people and animals allows targeted placement of scents in close proximity to the olfactory system to provide the continuous, stimulating, relaxing, therapeutic and/or medicinal effects desired by the aromatherapist. The inventive system comprises a sewn, double-layered pouch of vapor-permeable material with sealable opening for inserting aromatic sachet materials, either loose or contained in a small bag. The device thus filled with aromatics is worn around the neck, wrist or leg, and is retained in place by suitable attachment device such as hook and loop strips. The preferred bandana-shaped embodiment is generally triangular with elongated tabs extending from opposed apexes in which the third (depending) apex of the pouch contains the replaceable sachet mixture. Aromatic vapors are diffused through the air at normal temperatures or activated through other means, such as through body heat generated by exercise or by manual kneading or squeezing of the pouch.

13 Claims, 5 Drawing Sheets

U.S. PATENT DOCUMENTS

| | | |
|---|---|---|
| D206,749 S | 1/1967 | Klimkiewicz |
| D206,861 S | 2/1967 | Klimkiewicz |
| 3,477,409 A | 11/1969 | Costanzo |
| 3,605,121 A | 9/1971 | Suzuki |
| 3,814,061 A | 6/1974 | Aries et al. |
| 4,031,859 A | 6/1977 | Stewart |
| 4,050,417 A | 9/1977 | Ellis |
| 4,091,766 A | 5/1978 | Colliard |
| 4,184,452 A | 1/1980 | Buzzell et al. |
| 4,193,986 A | 3/1980 | Cox |
| 4,208,986 A | 6/1980 | Costanzo |
| 4,218,991 A | 8/1980 | Cole |
| 4,225,578 A | 9/1980 | von Bittern et al. |
| 4,250,838 A | 2/1981 | Ott |
| 4,321,891 A | 3/1982 | Moeller |
| 4,502,265 A | 3/1985 | Horrigan |
| D289,454 S | 4/1987 | Taub |
| 4,671,960 A | 6/1987 | Thielen et al. |
| 4,713,291 A | 12/1987 | Sasaki et al. |
| 4,763,604 A | 8/1988 | Meekins |
| D297,776 S | 9/1988 | Bridges |
| 4,788,722 A | 12/1988 | Oliver |
| 5,025,508 A | 6/1991 | Duncan |
| 5,038,431 A | 8/1991 | Burgin et al. |
| 5,058,211 A | 10/1991 | Hanks |
| 5,109,803 A | 5/1992 | Dunham et al. |
| 5,144,913 A | 9/1992 | Yasui |
| 5,233,942 A | 8/1993 | Cooper et al. |
| 5,363,809 A | 11/1994 | Roe |
| 5,381,559 A | 1/1995 | Wakefield, III |
| 5,383,921 A | 1/1995 | Barry |
| 5,414,869 A | 5/1995 | Thomson |
| 5,450,820 A | 9/1995 | Kirsch |
| 5,465,689 A * | 11/1995 | Winder ................. 119/654 |
| 5,467,743 A | 11/1995 | Doose |
| 5,474,033 A | 12/1995 | Mitchell, Jr. |
| 5,503,114 A | 4/1996 | Castagna |
| 5,555,848 A | 9/1996 | Trujillo et al. |
| D381,786 S | 8/1997 | Arakawa |
| 5,655,272 A | 8/1997 | Young |
| 5,791,297 A | 8/1998 | Mudge |
| 5,794,572 A | 8/1998 | Saunders et al. |
| D397,835 S | 9/1998 | Inspector |
| 6,016,573 A * | 1/2000 | Olson ..................... 2/207 |
| 6,016,772 A | 1/2000 | Noyes |
| D423,150 S | 4/2000 | Vignere |
| 6,101,981 A | 8/2000 | Friend et al. |
| D433,863 S | 11/2000 | Rosenstadt et al. |
| 6,173,675 B1 | 1/2001 | Licciardo |
| 6,203,813 B1 | 3/2001 | Gooberman |
| 6,209,134 B1 | 4/2001 | Schiesel |
| 6,209,140 B1 | 4/2001 | Ebeling |
| 6,325,024 B1 | 12/2001 | Masukawa |
| 6,360,404 B1 | 3/2002 | Mudge et al. |
| 6,418,881 B1 | 7/2002 | Starratt |
| D475,163 S | 5/2003 | Huber |
| 6,557,497 B1 | 5/2003 | Milligan |
| 6,588,376 B1 | 7/2003 | Groh |
| 6,626,536 B2 * | 9/2003 | Mesplay .................. 351/203 |
| 6,635,344 B1 | 10/2003 | de Almeida et al. |
| 6,640,715 B1 | 11/2003 | Watson et al. |
| 6,675,744 B1 | 1/2004 | Levan |
| D490,193 S | 5/2004 | D'Anza |
| 6,763,785 B1 | 7/2004 | Grady |
| 6,802,282 B2 | 10/2004 | Muckleroy |
| 6,834,847 B2 | 12/2004 | Bartsch et al. |
| 2003/0045447 A1 | 3/2003 | Heibel et al. |
| 2004/0247528 A1 * | 12/2004 | Schoneberg ................. 424/40 |
| 2005/0118383 A1 * | 6/2005 | Cargill et al. ................. 428/68 |

FOREIGN PATENT DOCUMENTS

JP          2003 230472          8/2003

* cited by examiner

AROMATHERAPY DELIVERY SYSTEM

CROSS REFERENCE TO RELATED APPLICATIONS

This application is the Regular US Application of prior Provisional Application Ser. No. 60/554,567 filed Mar. 19, 2004 under the same title by the same inventors, the filing date of which is claimed for priority under 35 US Code §§ 119(e) and 120.

FIELD

The invention relates to an aromatherapy delivery system, and more particularly to an inventive device worn around the necks of people or animals to deliver aromatic and/or medicinal treatment vapors for aromatherapy and inhalation psychological and physiological treatment.

BACKGROUND

Aromatherapy is the use of aromatic and/or medicinal vapors to enhance a feeling of well-being and for therapeutic effects. Aromatherapy has been practiced by humans for thousands of years as a mode of healing and relaxation. It is believed that aromatherapy originated with the Egyptians more than 4000 years ago. The Egyptians used aromatic plants to create aromatic massage oils, medicines, skin care products, perfumes and cosmetics.

Aromatherapy has gained in popularity and in credence in holistic medicine as a mode of healing and relaxation for increasingly busy lives. Fragrant essential oils are used in either liquid or vapor form. Hydrosols may be similarly used as essential oils. In addition, some hydrosols possess unique characteristics that may be different from essential oils. The dried plant material contained in a sachet contains the qualities and components of its essential oil and/or hydrosol in an unextracted and unadulterated form.

Most of the fragrant material used in aromatherapy is plant-based and requires drying to prevent mold growth and deterioration. Leaves, flowers, stems, seeds, bark or roots are used either in whole or part.

The oils can enter the body via the skin or the olfactory system. Essential oils can be absorbed through the skin in an effort to cleanse, nourish, and rejuvenate the body and/or to heal burns, cuts and ease irritation. The essential oils also can diffuse through the air, enter the nose and stimulate the brain. The brain perceives the smell and registers an emotion. When the brain is stimulated by the same scent again, it associates the same emotion with the particular scent, and the same emotion is felt again.

It is widely accepted that the use of certain herbs positively affects psychological and physiological functioning. As essential oils are inhaled, they pass over the olfactory bulb where they fit into tiny receptors, sending a nerve message or electrical signal to the limbic system. The first stops are the amygdala and hippocampus, the memory centers of the brain. If a memory has previously been tagged by these fragrances, the aroma can trigger an emotional flashback (this is aromacology; a unique response to a scent, triggered by memory). Certain essential oils evoke an aromatherapy response that is the same in all people. The message travels on to the hypothalmus which acts as a relay station, sending the scent to various other parts of the brain to trigger responses of euphoria, clarity, calm, etc.

Studies suggest that the aromatic oils stimulate the body's own immune system, resulting in a quick therapeutic response. Indeed, recent research on the migration of large molecules or particulates to the brain via the olfactory nerve system indicates there is a substantial scientific basis for the benefits of aromatherapy. Deeper breathing, which is induced by aromatherapy, also assists in oxygenation of the blood and may serve to improve overall cardiovascular health.

Aromatherapy for animals has also become recognized as legitimate and beneficial as human awareness of animal stress and boredom increases. We recognize stress imposed on animals, resulting, for example, from being left alone for long periods of time, or from the monotonous existence inside zoo enclosures or homes for that matter. We also have a greater awareness that animals suffer from a variety of medical conditions, including a wide range of skin conditions.

Aromatherapy is used to assist animals with various ailments, including flea and tick control, parasite control, burns, itching, arthritis, cuts, and car sickness. Essential oils used on animals include Tea Tree Oil, Peppermint, Lavender, and Eucalyptus. Tea Tree Oil is used as an antibacterial, antifungal, and antiviral agent. It is soothing to skin irritations such as insect bites and eczema. Peppermint is useful to prevent motion sickness and nausea, and is effective in discouraging insects. Lavender is calming, anti-depressive, anti-inflammatory, and helpful for treating burns. It is useful as a fungicide and germicide. Eucalyptus is bactericidal, antifungal, and a useful inhalant for respiratory complaints.

Current methods for applying aromatic essential oils to animals include: direct application to the skin via sprays, shampoos, soaps, applying drops to an animal's bedding, padding, or crate, and/or rubbing the oils into the skin or on the foot pads of the animal.

These methods are limited for a number of reasons, including that the animal must be in the location where the essential oils have been applied in order to achieve any benefit. In the case of shampoos or sprays applied directly to the animal, the therapeutic effect of the essential oils reaching the animal's olfactory system is often quickly lost due to animal behavior, such as a dog who has been shampooed who proceeds immediately to shake itself or roll in dirt, or a cat that licks itself clean. Moreover, natural animal skin oils (created as part of the animal's system for keeping its fur clean) tend to mask the beneficial scent of any human-applied essential oils applied directly to the animal's skin.

Current methods for applying essential oils to humans have similar drawbacks. For example, aromatherapy conducted at spas can only result in benefits at the spa location. Aromatherapy devices used privately in the home also are limited to the home setting. If essential oils are applied directly to a person's skin (such as is done for perfumes), the person must "wear" that particular scent until the essential oil is washed off. This causes problems with others who may be sensitive to strong aromas, or problems with inappropriate settings, such as "wearing" the aroma while the person is at work.

Accordingly, there is a need in the field for an improved aromatherapy delivery system for persons and animals.

THE INVENTION

Summary, Including Objects and Advantages

The inventive aromatherapy delivery system for people and animals comprises a double-layered pouch of pliable, vapor-permeable material containing aromatic and/or medicinal materials inserted between the layers that is worn around the neck, wrist or leg and is retained in place by suitable attachment device such as hook-and-loop strips (such as Velcro® brand). When worn around the neck of pets, the attachment device may be worn on the chest, side, shoulders, or back of the animal and preferably provides for safe release in the event the device catches on an object.

The aromatic and/or medicinal materials emit inhalation treatment vapors that have a relaxing and/or pleasing effect on the wearer of the device, and/or provide a therapeutic benefit as a result of being inhaled through the person or animal's olfactory and respiratory systems. The aromatherapy device moves with the person or animal thereby providing active, as opposed to merely passive, aromatherapy benefit.

The preferred shape of a first embodiment is that of a "bandana" (generally triangular with elongated tabs extending from opposed apexes). The third (depending) apex of the pouch contains a sachet mixture of scented aromatherapy material providing aromatherapy to the wearer of the device.

The dried sachet mixture can be loose inside the pouch or can be contained in an internal, vapor-permeable sack or bag (similar to a tea bag). The pouch can be permanently stitched closed, or can be openable through releasable/resealable attachment strips between layers of the pouch, or a horizontally oriented zipper opening. These features thereby permit insertion and removal of sachet mixtures or other substances of therapeutic benefit in either loose form or in pre-assembled vapor permeable bags and permits removal of the sachet mixture for cleaning of the pouch or replacement with a fresh or different aromatic/medicinal material.

In one embodiment for animals (pets), the name of the pet (or other identifying indicia) is stitched to the outside of the device to identify the delivery device's wearer. This provides pet owners with the opportunity to make a fashion statement and personal statement about their pets.

BRIEF DESCRIPTION OF THE DRAWINGS

The invention is described in detail by reference to the following figures.

DETAILED DESCRIPTION OF THE INVENTION, INCLUDING THE BEST MODE

The following detailed description illustrates the invention by way of example, not by way of limitation of the scope, equivalents or principles of the invention. This description will clearly enable one skilled in the art to make and use the invention, and describes several embodiments, adaptations, variations, alternatives and uses of the invention, including what is presently believed to be the best modes of carrying out the invention.

In this regard, the invention is illustrated in the several figures, and is of sufficient complexity that the many parts, interrelationships, and sub-combinations thereof simply cannot be fully illustrated in a single patent-type drawing. For clarity and conciseness, several of the drawings show in schematic, or omit, parts that are not essential in that drawing to a description of a particular feature, aspect or principle of the invention being disclosed. Thus, the best mode embodiment of one feature may be shown in one drawing, and the best mode of another feature will be called out in another drawing.

The figures are numbered and annotated so that one skilled in the art, by reference to the numbered parts, will easily be able to understand the materials and method of use of the device and will be able to make and use the inventive aromatherapy delivery system to achieve the functionality described.

Figure 1:
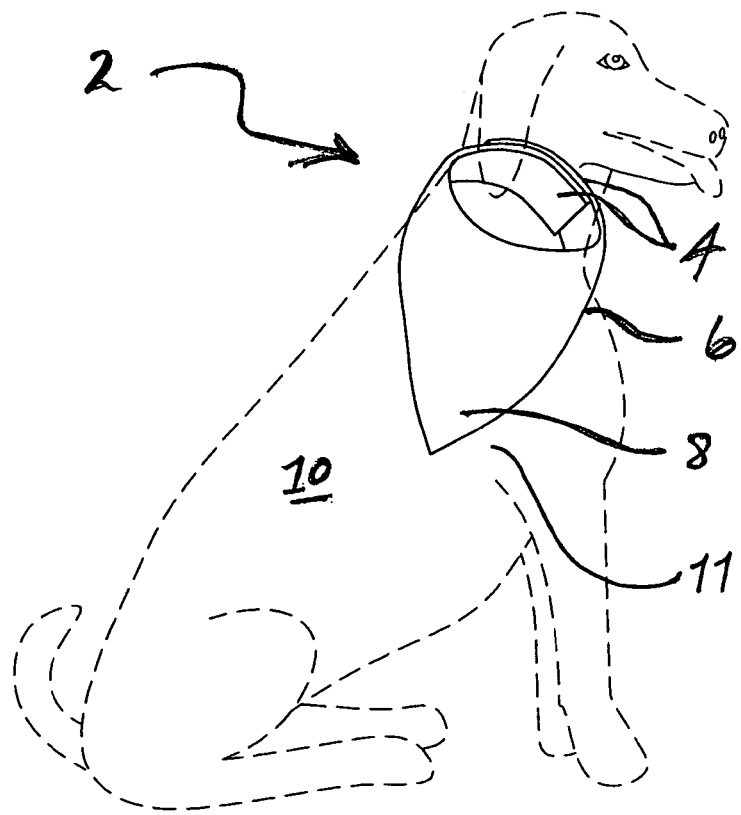
FIG. 1 is a schematic drawing showing a dog wearing a first, preferred embodiment of the inventive aromatherapy delivery system around its neck.
Figure 2:
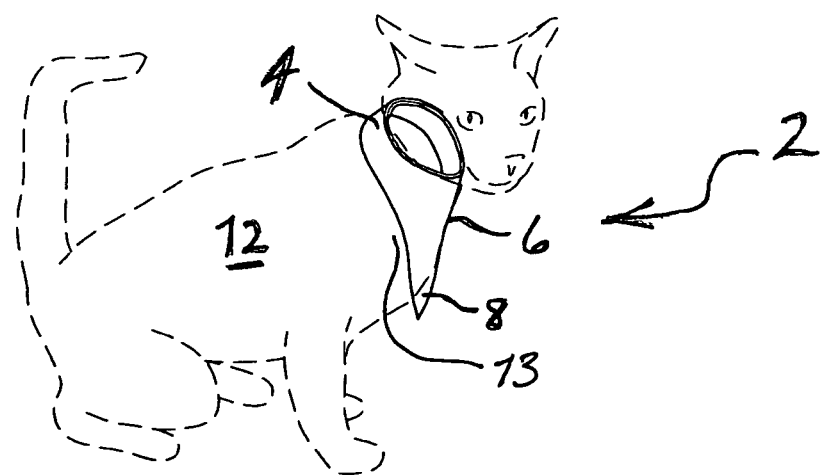
FIG. 2 is a schematic drawing showing a cat wearing a first, preferred embodiment of the inventive aromatherapy delivery system around its neck.

FIGS. 1 and 2 are schematic drawings showing the inventive aromatherapy delivery system 2 in use. By way of example only, FIGS. 1 and 2 show a dog 10 (FIG. 1) and cat 12 (FIG. 2) wearing the inventive aromatherapy delivery system 2 around their necks. FIG. 1 shows the straps of the device overlapping on the rear or side of the animal's neck facing away from the viewer, and the apex of the pouch resting on one shoulder of the animal. FIG. 2 shows the straps of the device overlapping on the back of the animal's neck, and the apex of the pouch hanging at the animal's chest.

Referring to both FIGS. 1 and 2, the device comprises a bandana-shaped, draping pouch 6 with two overlapping straps 4 extending from respective opposed apexes of the generally equilaterally triangular pouch body. The straps 4 are sufficiently long to encircle the animal or person's neck and overlap. The straps 4 are secured to each other by hook-and-loop strips (shown in FIGS. 3-6) to retain the inventive aromatherapy delivery system 2 in place. The inventive aromatherapy delivery system 2 may also be worn on an arm (wrist or biceps) or leg (ankle).

The delivery system device 2 is bandana-shaped, by which is meant an inverted generally triangular shape, and having straps 4 from upper corners 7, 9 (FIG. 5) and a pointed apex 8. In FIG. 1, the apex 8 is shown resting on the shoulder 11 of the dog 10; in FIG. 2, the apex 8 is shown resting on the chest 13 of the cat 12.

Figure 7:
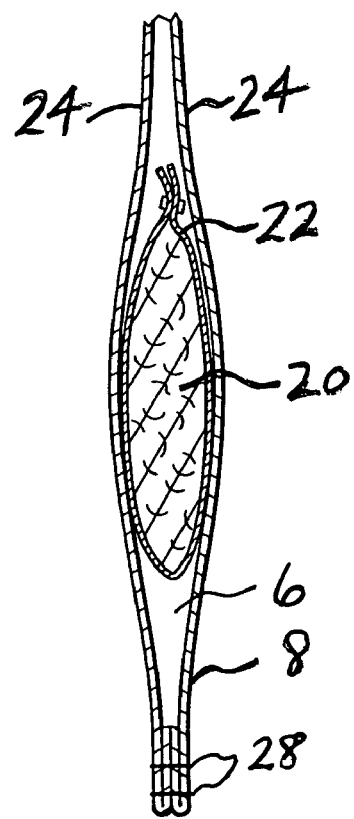
FIG. 7 is a cross-sectional side elevation view of the pouch apex of the aromatherapy delivery system showing the two external permeable layers and sachet materials retained inside an internal sack or small pouch.
Figure 8:
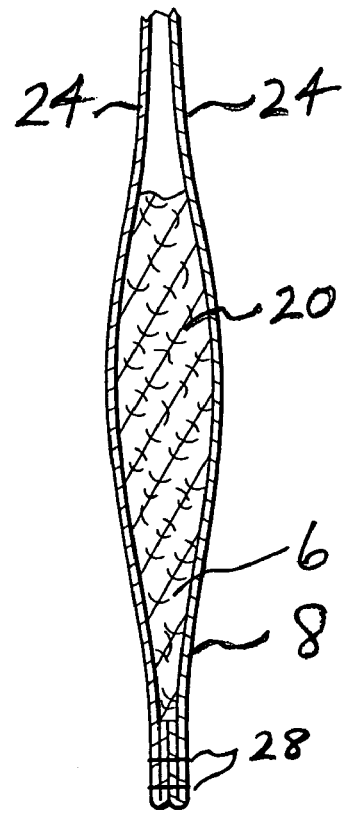
FIG. 8 is a cross-sectional side elevation view of the pouch apex of the aromatherapy delivery system showing a second embodiment in which the sachet materials are loose; and, FIG. 9 is a cross-sectional side elevation view of the top of the pouch of the aromatherapy delivery system showing a third alternate closure embodiment.

As shown in FIGS. 7 and 8, the delivery system device 2 is made of two spaced layers of pliable, vapor permeable material 24 sewn, fused, bonded, or otherwise adhered at the edges, thereby creating a pouch 6 for retention of aromatherapy materials, such as a dried sachet mixture 20. If sewn together, the stitching construction 28 along the edges of the pouch 6 can be of any type suitable for retention of the sachet mixture 20 inside the pouch 6, such as an exposed, stitched 28 and pinked seam allowance, or a concealed seam allowance created by stitching, reversing the two spaced layers 24 after stitching, and even top-stitching through the four resulting layers of fabric.

In the usual orientation shown in FIGS. 1 and 2, the sachet materials 20 gravitate to the apex 8 (shown in cross-section in FIGS. 7 and 8) and, as such, are in close proximity to the animal or person's face for breathing of the inhalation treatment vapors into the lungs and olfactory system. The vapors also may trigger taste receptors in the mouth.

Figure 3:
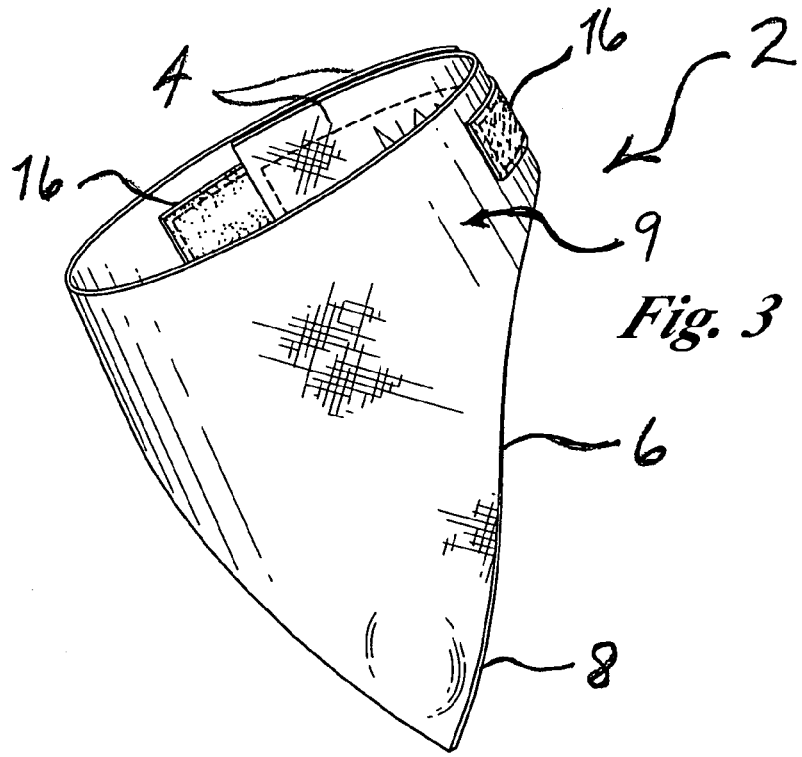
FIG. 3 is an isometric, ¾ front elevation view showing the inventive aromatherapy delivery system as worn.
Figure 4:
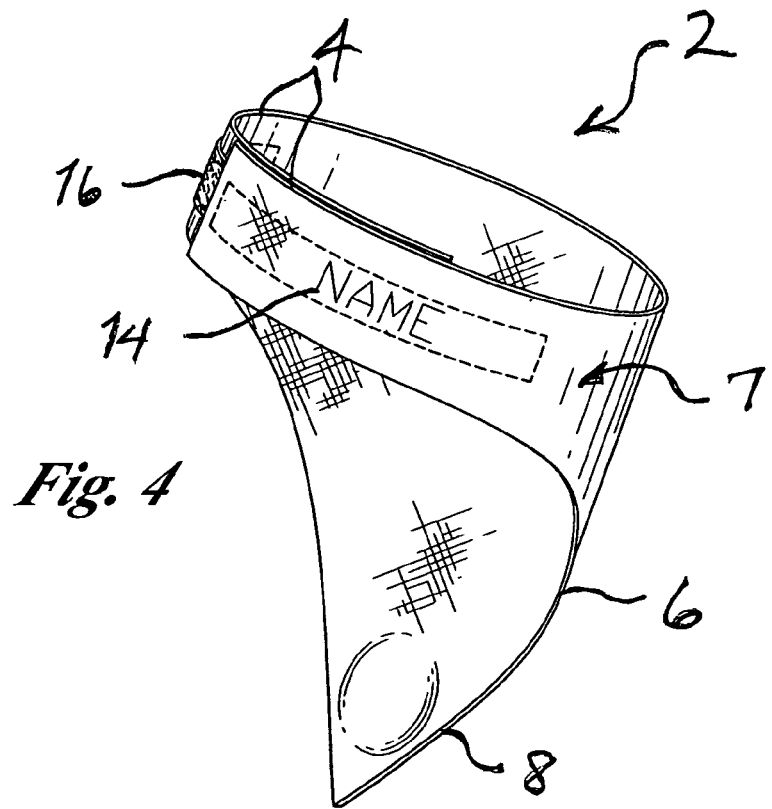
FIG. 4 is an isometric, ¾ rear elevation view showing the inventive aromatherapy delivery system of FIG. 3 from the back.

FIGS. 3 and 4 are isometric drawings showing opposed side views of the inventive aromatherapy delivery system 2 as worn around the neck of a person or animal. Referring to FIG. 3, the straps 4 of the device 2 overlap and are retained in position by cooperatively inter-engaging hook-and-loop strips 16. The sachet mixture 20 (shown in FIGS. 7 and 8) is inside the pouch apex 8 with the pouch 6 hanging down in bandana-fashion. As shown in FIG. 4, the device 2 may optionally include identification indicia 14 of the device's wearer (e.g., a pet's name) stitched, embroidered, or otherwise affixed to the externally-viewable portion of one or more of the device's 2 securing straps 4 or elsewhere on the device 2.

The device 2 may be made out of two layers of any pliable material, preferably a fabric, provided that at least a portion of the material used is sufficiently permeable to allow for the external diffusion of scent from inside the pouch 6. The two layers can be the same material, or different material (e.g., reversible, or to serve different functions to the wearer). The shape of the pouch apex 8 can be pointed, as shown in FIGS. 3 and 4, or any other desired shape. The straps 4 of the device 2 may be of any length or width sufficient to keep the device 2 around the wearer's neck and can be attached through use of hook-and-loop strips 16 or any other attachment device such as buttons, hooks, snaps, buckle, or the like. The device 2 can be worn externally (on animals or people) or under clothing (such as in the fashion that cravats are worn).

Although the examples illustrated in the drawings show the aromatherapy delivery system worn around the neck, it should be understood that it can be worn on other areas of the body, including, for example, the wrist, ankle, above the biceps, or waist.

Figure 5:
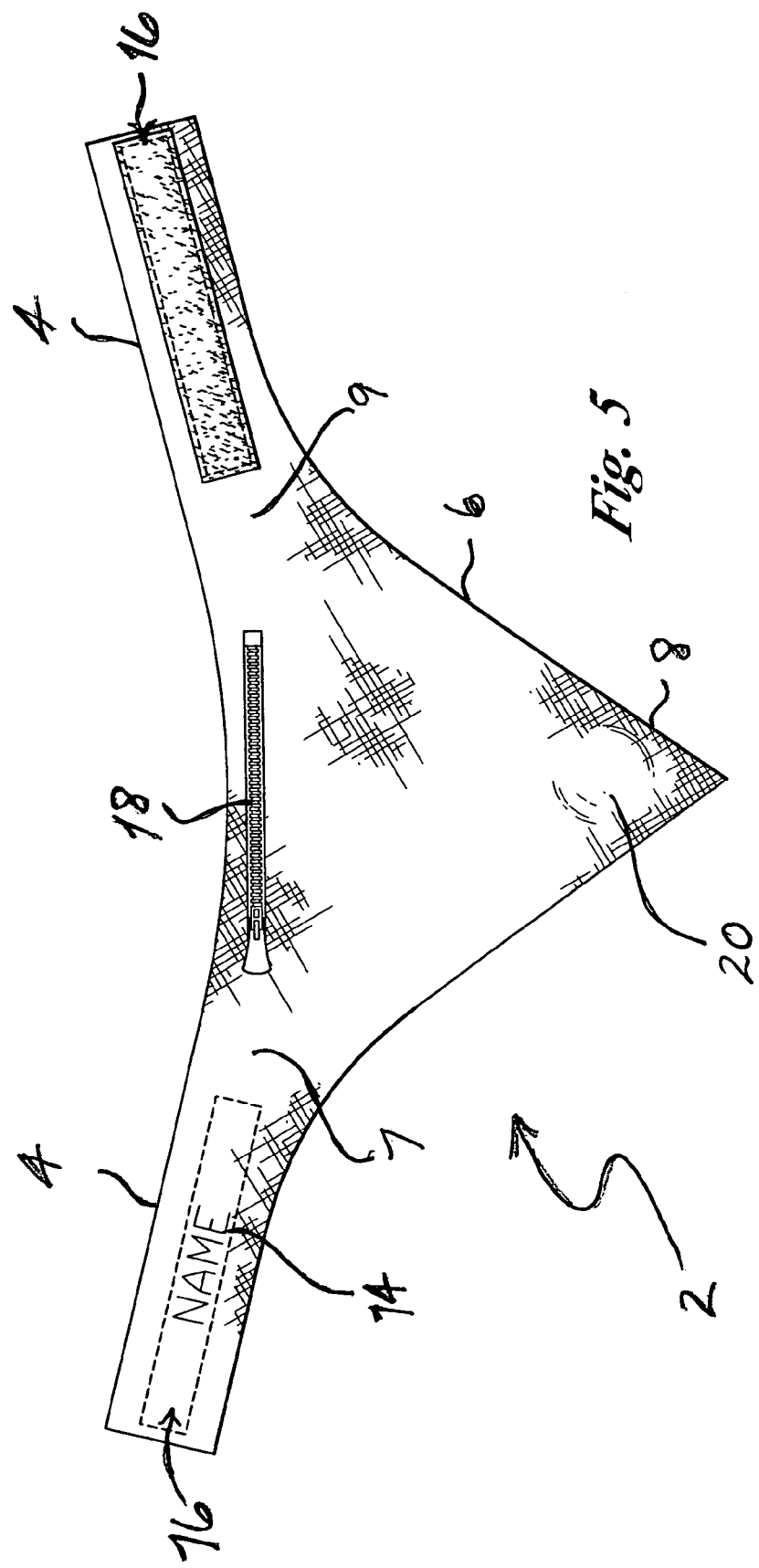
FIG. 5 is a back side plan view of the inventive aromatherapy delivery system in an extended, un-worn position.

FIG. 5 is a back side plan view of the inventive aromatherapy delivery system 2 in an extended, un-worn position showing the two straps 4 extending from opposed apexes of the generally equilaterally triangular body, with corresponding hook and loop strips 16 and optional stitched name 14, and showing an optional horizontally-oriented zipper closure 18 for insertion and removal of sachet materials 20 into and out of the pouch 6. The zipper closure 18 needs to be wide enough and long enough for insertion and removal of the sachet mixture 20 or internal sack 22 containing sachet mixture 20 (as shown in FIG. 7.)

Referring to FIG. 5, the zipper closure 18 is oriented horizontally between the upper corners 7, 9 of the device 2, and acts as a stiffener to assist in retaining the shape of the pouch 6. The zipper closure 18 is oriented horizontally and positioned near the upper corners 7, 9 to permit the opening or closure of the zipper 18 without interfering with the retention of the sachet mixture 20 inside the apex 8 of the pouch 6. The zipper closure 18 is positioned to permit opening and closure without catching on sachet mixture 20, without catching on an internal sack 22 (shown in FIG. 7), and so as to not allow loosely-retained sachet mixture 20 to escape from the apex 8 of the pouch 6.

Referring to FIG. 5, any closure device that allows for insertion and removal of aromatic materials can be used, including the shown zipper closure 18 or hook-and-loop strips 16.

Figure 6:
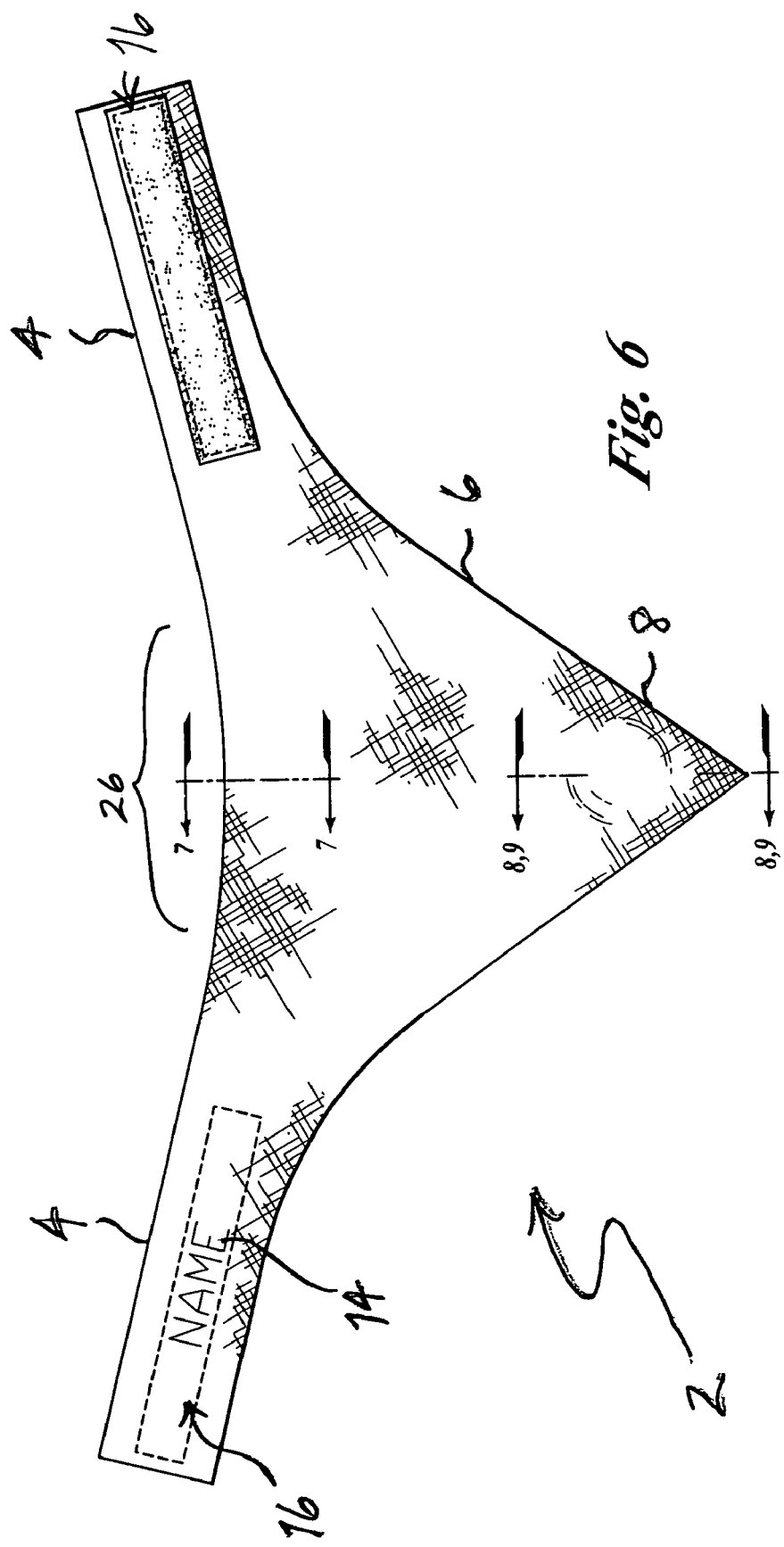
FIG. 6 is a front side plan view of the inventive aromatherapy delivery system of FIGS. 1-5 in an extended, un-worn position, showing cross-sectional view orientations for FIGS. 7, 8 and 9.
Figure 9:
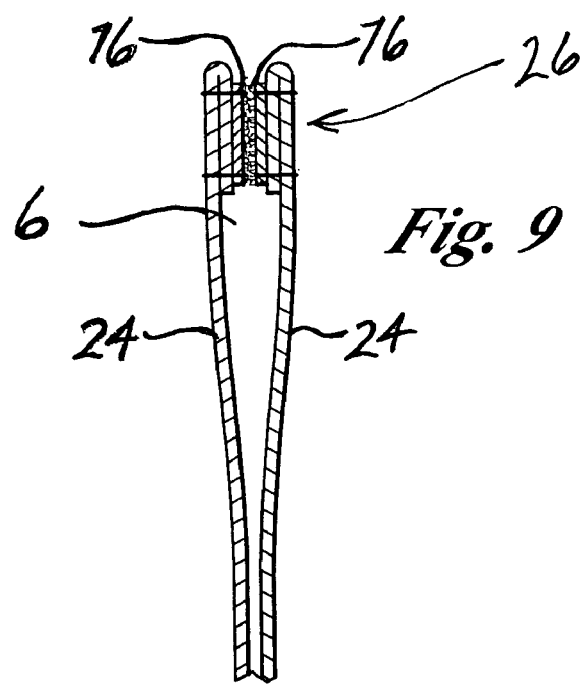

FIG. 6 is a front plan view of the inventive aromatherapy delivery system 2 in an extended, un-worn position, showing cross-sectional view orientations for FIGS. 7, 8 and 9.

FIG. 7 is a cross-sectional side elevation view of the pouch apex 8 showing two external pouch material layers 24 and sachet mixture 20 retained inside an internal sack 22. The internal sack 22 may be made of any material that allows for diffusion of the scent vapors and/or essential oils from the sachet mixture 20. The internal sack 22 may be porous, flexible, and made of fabric that may be sewn or fused at its edges by heat, pressure or bonding material. In the preferred embodiment, the internal sack 22 comprises a pre-assembled bag of dried herbs or other aromatherapy materials for insertion in the pouch 6 of the device 2.

If desired, the wearer of the device (or caretaker in the case of an animal) may remove and replace the internal sack 22 (e.g., through use of a zipper closure 18 shown in FIG. 5 or the hook-and-loop 16 closure shown in FIG. 9) to change the sachet mixture 20 when the sachet mixture 20 loses its potency, when the wearer desires a different scent, and/or when the device 2 needs to be cleaned or washed.

FIG. 8 is a cross-sectional side elevation view of the pouch apex 8 showing an alternate embodiment wherein the sachet materials 20 are loose between the two external pouch material layers 24. This embodiment may allow for greater diffusion of the vapors and/or essential oils due to the free movement of the sachet mixture 20 within the pouch apex 8.

The following is a non-exhaustive list of plant-based materials that may be used alone or in combination as a dried sachet mixture 20 in the aromatherapy delivery system 2. The substances listed are known or believed by aromatherapists and herbalists as emitting inhalation treatment vapors possessing healing, relaxing or potential medicinal benefits based on the substances' chemical properties and/or fragrance:

COMMON NAME—SCIENTIFIC NAME

Allspice (Pimento)—*Pimenta officinalis*
Aloe—*Aloe vera* or *Aloe barbadensis*
Angelica—*Angelica archangelica*
Anise—*Pimpinella anisum*
Anise Hyssop—*Agastache foeniculum*
Apple Mint—*Mentha suaveolens*
Azores Thyme—*Thymus caespititius*
Basil, Sweet—*Ocimum basilicum*
Bay, Sweet—*Laurus nobilis*
Bee Balm—*Monarda species*
Benzoin—*Styrax benzoin*
Bergamot—*Citrus bergamia*
Blackberry—*Rubus species*
Bois de Rose (Rosewood)—*Aniba rosaeodora*
Borage—*Borago officinalis*
Cajeput—*Melaleuca leucadendron*
Calendula—*Calendula officinalis*
Caraway—*Carum carvi*
Cardamom—*Elettaria cardamomum*
Catmint—*Nepeta faassenii*
Catnip—*Nepeta cataria*
Cedarwood—*Cedrus atlantica*
Celery—*Apium graveolens*
Caraway-Scented Thyme—*Thymus herba-barona*
Chamaemelum nobile—*Anthemis nobilis*
Chamomile—*Matricaria recutita*
Chicory—*Cichorium intybus*
Costmary—*Chrysanthemum balsamati*
Cinnamon Bark and Leaf—*Cinnamomum zeylanicum*
Clary Sage—*Salvia sclarea*
Clove—*Eugenia caryophyllata*
Clover—*Trifolium pratense, T. repens* and *T. fragiferum*

Coffee beans
Coriander (Cilantro, Chinese Parsley)—*Coriandrum sativum*
Cubeb—*Piper cubeba*
Cumin—*Cuminum cyminum*
Cypress—*Cupressus sempervirens*
Dandelion—*Taraxacum officinale*
Dill—*Anethum graveolens*
Eucalyptus (Blue Gum)—*Eucalyptus globulus*
Eucalyptus (Lemon Scented Gum)—*Eucalyptus citriodora*
Echinacea—*Echinacea angustifolia* and *Echinacea purpurea*
Evening Primrose—*Oenothera biennis*
Fennel—*Foeniculum vulgare*
Feverfew—*Tanacetum parthenium*
Frankincense—*Boswellia thurifera*
Garlic—*Allium sativum*
Geranium—*Pelargonium graveolens, P. tomentosum, P. crispum,* and *P. nervosum*
Ginger—*Zingiber officinale*
Ginkgo—*Ginkgo biloba*
Ginseng—*Panax quinquefolium*
Ginseng, Korean—*Panax ginseng*
Ginseng, Siberian—*Eleutherococcus senticosus*
Golden Apple Mint—*Mentha gentilis*
Grapefruit—*Citrus paradisi*
Hop—*Humulus lupulus*
Horehound—*Marrubium vulgare*
Hyssop—*Hyssopus officinalis*
Jasmine—*Jasminum officinale*
Juniper Berries—*Juniperus communis*
Kava—*Piper methysticum*
Lavender (Hybrids)—*Lavandula intermedia*
English Lavender—*Lavandula angustifolia* (*L. officinalis, L. spica, L. vera*)
French Lavender—*Lavandula dentata*
Spanish Lavender—*Lavandula stoechas*
Spike Lavender—*Lavandula latifolia*
Lemon—*Citrus limonum*
Lemon Balm and Melissa—*Melissa officinalis*
Lemongrass—*Cymbopogon citratus*
Lemon Thyme—*Thymus x citriodorus*
Lemon Verbena—*Lippia citriodora*
Licorice—*Glycyrrhiza glabra*
Lime—*Citrus limetta*
Mandarin—*Citrus nobilis*
Marigold—*Tagetes patula*
Marjoram—*Origanum maijorana*
Marsh Mallow—*Althaea officinalis*
Mint—*Mentha* species
Mother-of-Thyme—*Thymus serpyllum*
Mullein—*Verbascum thapsus*
Myrrh—*Commiphora myrrha*
Myrtle—*Myrtus communis*
Nasturtium—*Tropaeolum majus*
Neroli—*Citrus aurantium*
Nutmeg—*Myristica fragrans*
Orange—*Citrus aurantium*
Oregano—*Origanum vulgare*
Palmarosa—*Cymbopogon martini*
Parlsey—*Petroselinum crispum*
Passionflower—*Passiflora incarnata*
Patchouli—*Pogostemon patchouli*
Pennyroyal, American—*Hedeoma pulegioides*
Pennyroyal, European—*Mentha pulegium*
Peppermint—*Mentha x piperita*
Peru Balsam—*Myroxylon pereirae*
Petigrain—*Citrus bigarade*
Pine—*Pinus sylvestris*
Plantain—*Plantago major*
Rose—*Rosa* species inclusive of *Rosa centifolia, R. damascena, R. multiflora, R. chinensis, R. chinensis minima, R. alba* and *R. gallica*
Rosemary—*Rosmarinus officinalis*
Rue—*Ruta graveolens*
Sage—*Salvia officinalis*
Sandalwood—*Santalum album*
Summer Savory—*Satureja hortensis*
Saw Palmetto—*Serenoa repens*
Slippery Elm—*Ulmus rubra*
Spearmint—*Mentha spicata*
Spruce—*Picea mariana*
St. John's Wort—*Hypericum perforatum*
Strawberry—*Fragaria vesca*
Tarragon, French—*Artemisia dracunculus 'sativa'*
Tea Tree—*Melaleuca alternifolia*
Thyme—*Thymus vulgaris*
Tolu Balsam—*Myroxlon toluiferum*
Valerian—*Valeriana officinalis*
Vetiver—*Vetiveria zizanoides*
Violet—*Viola odorata*
Vitex (Chastetree)—*Vitex agnus-castus*
Wild Yam—*Dioscorea villosa*
Winter Savory—*Satureja montana*
Witch Hazel—*Hamamelis virginiana*
Yarrow—*Achillea millefolium*
Ylang-Ylang—*Cananga odorata*

This list of plant-based, natural herbals and traditional aromatherapy compounds and compositions is not exclusive; other naturally-produced substances with positive therapeutic benefits when introduced to the olfactory system may be used, and other such substances may be discovered or researched through use of the inventive device 2 in the future.

In addition, any other pleasant or favorite aromatic materials may be used to induce positive emotions in the wearer, and/or trigger pleasant memories. Examples include chocolate, bread, coffee, vanilla and the like.

The sachet mixture 20 also may comprise medicinals, such as menthol, eucalyptol, or any drug substance of any particulate size that is known or believed to provide therapeutic benefit through inhaling of vapors into the lungs and olfactory system or impingement on the oral mucosa (lingual system) of the device wearer. The inventive device 2 may be used to research the potential therapeutic benefits of man-made substances either alone or in combination with naturally-made substances as a result of the substance(s) delivery to the respiratory and/or olfactory systems. The therapeutic benefit of the substance delivery may end at the respiratory and/or olfactory systems, or may extend and flow to other bodily systems, including without limitation, the brain, other parts of the nervous system, and/or the circulatory system.

The sachet mixture 20 may be incorporated into various inert carriers, including without limitation, organic or inorganic materials such as zeolites, granular materials, charcoal, talc, powdered clay, porous plastics/ceramics, or sponge-like foams.

FIG. 9 is a cross-sectional side elevation view of the top margin of the pouch 26 in the area between the two straps (see FIG. 6) showing an alternate embodiment comprising corresponding hook-and-loop strips 16 affixed to the internal side of each pouch layer 24 at the top margin of the pouch 6. When opened, the wearer (or animal caretaker) may insert sachet mixture 20 (shown in FIGS. 7 and 8) into the pouch 6 and then close the pouch 6 by pressing the hook-and-loop strips 16 together. Likewise, the sachet materials 20 can be removed, refreshed or replaced through the hook-and-loop closure 16.

Any attachment device that keeps the sachet mixture inside the pouch 6 could be used.

The shape of the pouch 6 and straps 4 can be individually designed to provide the wearer with means for making a fashion and/or personal statement.

INDUSTRIAL APPLICABILITY

It is clear that the inventive aromatherapy delivery system of this application has wide applicability to the aromatherapy industry, namely by providing people and animals with a convenient, comfortable, and fashionable aromatherapy delivery system that provides soothing, relaxing scents in close proximity to the olfactory and respiratory systems. The sachet mixture may be easily replaced when it loses its potency or depending on the desires of the wearer for different scents. The device may be easily removed when other people are in close proximity (such as during work hours), and then quickly and easily replaced when appropriate (such as over a lunch hour or when driving to or from work). The fashion characteristics of the system afford the wearer privacy, dignity and comfort that may help overcome the wearer's feelings of anxiety, stubbornness or disinterest associated with undergoing a therapeutic or medicinal application.

In addition, the device can have a wide range of designs to provide the functionalities disclosed herein. For example, the pouch of the device could be sized and shaped differently for people as opposed to different animals (dogs, cats, zoo animals), and differently for men, women and children. The two fabrics can be different colors and/or patterns on the exposed sides (FIGS. 5 and 6) for more variety and fashion coordination.

The sachet mixture aromatic vapors are diffused through the air at normal temperatures or could be activated through other means, such as through body heat generated by exercise or by manual kneading or squeezing of the pouch. The sachet mixture can contain medicinals or other substances as recommended by aromatherapists for providing therapeutic benefit through inhalation.

In another embodiment, the vapor molecule of the aromatic material may be modified, e.g., chemically reacted in advance, with an olfactory medicinal or therapeutic compound, so that the aroma vapor functions as a carrier of the therapeutic material for vapor delivery to the olfactory mucosa or nerves.

This invention is therefore to be defined as broadly as the prior art will permit, and in view of the specification if need be, including a full range of current and future equivalents thereof.

Parts List: This list is provided as an aid to examination and may be canceled upon allowance.

| 2 | inventive aromatherapy delivery system |
| --- | --- |
| 4 | straps |
| 6 | pouch |
| 7 | upper corner |
| 8 | pouch apex |
| 9 | opposed upper corner |
| 10 | dog |
| 11 | dog's shoulder |
| 12 | cat |
| 13 | cat's chest |
| 14 | stitched or embroidered word |
| 16 | hook-and-loop strip |
| 18 | zipper closure |
| 20 | sachet mixture |
| 22 | internal sack containing sachet mixture |
| 24 | external material layers of pouch |
| 26 | top margin of pouch |
| 28 | stitching |

The invention claimed is:

1. An aromatherapy delivery product for delivery of inhalation treatment vapors to a person or an animal's olfactory and respiratory systems consisting of:
  a) two spaced layers of pliable fabric material having a main body portion that is generally triangular in shape, and at least a portion of said material is sufficiently permeable to permit the external diffusion of the inhalation treatment vapors;
  b) said two layers of pliable material are aligned with one layer disposed congruently over the other layer and secured together along at least adjacent marginal edges to create a generally triangular pouch therebetween containing dry aromatherapy material therein that emits inhalation treatment vapors, said pouch having an upper top margin, converging sides and a depending apex;
  c) said two layers of pliable material are secured together to form opposed securing straps formed as an integral lateral extension of said top margin to permit forming a bandana to be worn about the neck of a human or animal, and said permeable portion of said material is disposed in the area of said apex of said pouch;
  d) said pouch includes at least one horizontally-oriented full closure for internal access to the pouch formed in said triangular main body portion between said two fabric layers, said closure is positioned in proximity to the top margin of the pouch and spaced above said apex;
  e) said securing straps have a length selected to retain the pouch in proximity to said olfactory and respiratory systems when secured as a bandana around the neck of a human or animal user; and
  said dry aromatherapy material consisting essentially of dry lavender plant material from the genus *Lavandula* retained at said depending apex of the pouch so that inhalation treatment vapors are presented in close proximity to the olfactory and respiratory systems as they are emitted through said permeable material.

2. The aromatherapy delivery product of claim 1 wherein the horizontally-oriented closure is permanently closed after the aromatherapy material has been inserted into the pouch.

3. The aromatherapy delivery product of claim 1 wherein the horizontally-oriented closure comprises opposed, resealable hook and loop closure strips.

4. The aromatherapy delivery product of claim 1 wherein the horizontally-oriented closure comprises one or more zipper closures.

5. The aromatherapy delivery product of claim 1 wherein the two spaced layers of material are different so that the bandana is reversible.

6. The aromatherapy delivery product of claim 1 wherein one or more of the spaced layers includes pet identifying indicia.

7. The aromatherapy delivery product of claim 1 wherein the length of said securing straps permits said securing straps to encircle a neck of a person or animal.

8. The aromatherapy delivery product of claim 1 wherein said securing straps include hook and loop closure strips for overlapping securement, said securement being sufficient to retain the product in place during use but permitting tear-away release without injuring a wearer.

9. The aromatherapy delivery product of claim 8 wherein said securing straps include pet identifying indicia.

10. The aromatherapy delivery product of claim 1 wherein said aromatherapy material is retained within an internal sack at the apex of the pouch, and at least a portion of said internal sack is sufficiently permeable to permit the external diffusion of the inhalation treatment vapors.

11. The aromatherapy delivery product of claim 1 wherein said inhalation treatment vapors provide a healing and/or relaxing benefit to a wearer of the product.

12. The aromatherapy delivery product of claim 1 wherein said inhalation treatment vapors provide a medicinal or therapeutic benefit to a wearer of the product.

13. The aromatherapy delivery product of claim 1 wherein said dried lavender plant material is obtained from at least one *Lavandula* plant, selected from the species *Lavandula intermedia, Lavandula angustifolia, Lavandula officinalis, Lavandula spica, Lavandula vera, Lavandula dentata, Lavandula stoechas, Lavandula latifolia*, and hybrids thereof.

* * * * *